United States Patent [19]

Gerling et al.

[11] Patent Number: 5,644,042

[45] Date of Patent: Jul. 1, 1997

[54] PROCESS FOR PRODUCTION OF ALDOBIONIC ACID AMIDE

[75] Inventors: Klaus Guenther Gerling, Laatzen; Claudia Schreer, Schellerten; Petra Schwarz, Hanover; Kornelia Wendler, Sehnde, all of Germany

[73] Assignee: Solvay Pharma Deutschland GmbH, Hanover, Germany

[21] Appl. No.: 576,700

[22] Filed: Dec. 21, 1995

[30] Foreign Application Priority Data

Dec. 24, 1994 [DE] Germany ............... 44 46 632.3

[51] Int. Cl.⁶ ............... C07H 15/04; C07H 15/18; C07H 1/00
[52] U.S. Cl. ............... 536/17.5; 536/1.11; 536/4.1; 536/17.6; 536/18.2; 536/22.1; 536/53; 536/54; 536/122; 536/124
[58] Field of Search ............... 536/17.5, 18.2, 536/11.11, 4.1, 22.1, 54, 17.6, 122, 124, 53

[56] References Cited

U.S. PATENT DOCUMENTS

| 5,037,973 | 8/1991 | Meinetsberger ............... 536/53 |
| 5,401,426 | 3/1995 | Gerling et al. ............... 252/8.6 |
| 5,403,922 | 4/1995 | Garelli-Calvet et al. ............... 536/1.11 |

FOREIGN PATENT DOCUMENTS

| 312087 | 4/1989 | European Pat. Off. ............... 536/53 |
| 541467 | 5/1993 | European Pat. Off. ............... 536/1.11 |
| WO92/06601 | 4/1992 | WIPO ............... 536/1.11 |

*Primary Examiner*—Floyd D. Higel
*Attorney, Agent, or Firm*—Evenson, McKeown, Edwards & Lenahan P.L.L.C.

[57] ABSTRACT

A process for the preparation of aldobionamides directly from an aldobionic acid starting material, in which an aldobionic acid is reacted by removing water by azeotropic distillation to obtain an aldobionolactone. The aldobionolactone can then be reacted with amines without further purification or isolation steps to obtain the aldobionamide.

14 Claims, No Drawings

PROCESS FOR PRODUCTION OF ALDOBIONIC ACID AMIDE

BACKGROUND OF THE INVENTION

The application relates to a process for the preparation of aldobionamide.

U.S. Pat. No. 5,401,426 (counterpart of EP 569,869) discloses a process for the preparation of lactobionamide compositions in which lactobionolactone is reacted with the appropriate fatty amines in a lower alkyl alcohol solvent.

Published German Patent Application No. DE 1,155,771 discloses a process for the preparation of aldobionic acid alkylamides, in particular of maltobionic acid, lactobionic acid or cellobionic acid alkylamides, in which the corresponding acid lactones are reacted with alkylamines in a dimethylformamide solvent.

According to the prior art processes for the preparation of aldobionamide, aldobionolactone is always used as the starting compound. Therefore, in the prior art, aldobionolactone must be prepared first and isolated in a prior process step by removing water from the corresponding aldobionic acid. However, because of the applicational properties of aldobionamides, it would be advantageous to prepare aldobionamides directly from the aldobionic acids in a single-stage process.

SUMMARY OF THE INVENTION

It is therefore an object of the present invention to provide a process by which aldobionamides can be prepared directly from aldobionic acids.

This and other objects are achieved in accordance with the presently claimed invention by providing a process for the preparation of aldobionamide, comprising the steps of
a) mixing an aldobionic acid or an aldobionic acid solution with an organic solvent capable of forming an azeotrope with water,
b) removing water from the aldobionic acid by azeotropic distillation to obtain an aldobionolactone, and
c) reacting the aldobionolactone with an amine to obtain the aldobionamide.

DETAILED DESCRIPTION OF PREFERRED EMBODIMENTS

The invention thus relates to a process for the preparation of aldobionamide, wherein:
a) an aldobionic acid or an aldobionic acid solution is mixed together with an organic solvent capable of forming an azeotrope with water,
b) water is removed from the aldobionic acid by means of azeotropic distillation to give the aldobionolactone, and
c) the aldobionolactone is reacted with amines to give the aldobionamide.

According to the process of the present invention, a direct synthesis of aldobionamides from aldobionic acids is possible, without having to first isolate the intermediate product aldobionolactone. Since the isolation of aldobionolactone is unnecessary, the process according to the present invention is particularly simple and economical. Additionally, the process according to the present invention can be carried out either batchwise or, preferably, continuously.

According to the process of the present invention, the aldobionic acids can be used either directly as a solid substance or as a solution in water or an organic solvent. Aqueous aldobionic acid solutions are preferably used because such solutions, obtained from the synthesis of the aldobionic acids from the respective aldoses, may be used directly for further reactions to give the corresponding acid amides.

All known aldobionic acids, such as maltobionic acid, lactobionic acid or cellobionic acid, can be reacted according to the process of the present invention. Lactobionic acid is preferably reacted according to the process of the present invention to give the corresponding lactobionamides.

In process step a) of the present invention, aldobionic acid or an aldobionic acid solution is mixed with an organic solvent which forms an azeotrope with water. For example, alkyl alcohols, acetic esters or even cyclohexane can be used as organic solvents capable of azeotrope formation. Organic solvents selected from the group consisting of ethyl acetate, cyclohexane, 2-methoxyethanol and 2-ethoxyethanol are preferably used. 2-Ethoxyethanol is particularly preferred.

The process of the present invention is expediently carried out in such a way that in process step a), the aldobionic acid or the aldobionic acid solution is mixed with an at least equal amount, for example, 2 to 5 times the amount, by volume of an organic solvent which can form an azeotrope with water. The mixture is stirred for about 1 hour at an elevated temperature, e.g. 70° to 80° C.

Then, in process step b), an azeotropic distillation is carried out, optionally in a vacuum, separating off an azeotropic mixture of water and organic solvent as the distillate. If desired, the azeotropic distillation can be continued in order to complete the reaction of aldobionic acid into aldobionolactone. This is done by adding fresh organic solvent in amounts 0.3 to 2 times the volume of the mixture of organic solvent and aldobionic acid or aldobionic acid solution originally employed, after up to about 75% of the amount by volume of organic solvent initially introduced has been distilled off. The addition of fresh organic solvent can be repeated several times if desired. If possible, the azeotropic distillation is carried out until water is drained out of the mixture as completely as possible.

Then, in process step c), the desired amine is added to the suspension obtained from step b). The amine is added directly if it is a liquid, otherwise the amine is dissolved in the same organic solvent and then added. The mixture is stirred for at least 30 minutes or even longer at an elevated temperature, e.g. 40° to 50° C., and usually, a nearly clear solution is formed from the suspension. Subsequently, the mixture is additionally stirred for at least about 12 hours at room temperature. Then a further organic solvent, such as ethyl acetate, is added. A precipitate is deposited, which is filtered out, washed and then dried in a vacuum drying oven at room temperature, or preferably at 40° to 50° C. The yields of aldobionic acid alkylamide are usually in the range of from about 85 to 98% by weight.

Aldobionic acid alkylamides having alkyl chains of any desired chain length can be prepared according to the process of the present invention. However, alkylamines having an alkyl chain length of 8 to 18 carbon atoms are preferably used. Primary fatty amines which have been obtained from naturally occurring fatty acids are further preferred. Primary fatty amines of this type usually exist as mixtures of fatty amines of different chain length and usually also contain, in addition to saturated fatty amines, a proportion of monounsaturated to polyunsaturated fatty amines. In this case, the proportion of monounsaturated fatty amines can vary from between about 5 to 85% by weight. Examples of such fatty amine mixtures include coconut fatty amine from the fatty acid mixture derived from coconut fat, tallow amine and hydrogenated tallow amine from the fatty acid mixture derived from tallow, and oleylamine from the fatty acid mixture derived from sunflower oil and/or soya bean oil. In particular, fatty amines selected from the group consisting of coconut fatty amine, tallow amine, hydrogenated tallow amine and olaylamina can be used according to the process of the present invention.

In a preferred embodiment, the process according to the present invention is carried out in such a way that the azeotropic mixture distilled off in process step b) and the solvent mixture obtained in process step c) are combined and separated again into water and organic solvent components wherein the organic solvents are fed back into process step a) or c). The separation can in this case be carried out in a manner known in the art. For example, when using ethyl acetate as the organic solvent, the water-ethyl acetate mixture obtained can be distilled off, and the water phase can be separated from the ethyl acetate distillate by phase separation using a water separator or separating funnel. Other methods for water separation are also possible, such as separation by column distillation, extraction or continuous extraction.

By feeding the recovered organic solvents back into the process, the process can preferably be arranged in a continuous procedure as a largely closed cycle process in an economical and environmentally friendly manner. Since the process according to the present invention is carried out as a single-stage process without the need to isolate an intermediate, the process is a surprisingly simple way to obtain aldobionoamides directly from aldobionic acid starting compounds. Furthermore, as the organic solvents are fed back into the process continuously, the accumulation of relatively large solvent residues, which have to be disposed of, is avoided.

The following examples are intended to illustrate the invention further, but without restricting its scope.

EXAMPLES

As an example, the process according to the present invention for the preparation of aldobionamide is illustrated by the preparation of lactobionic acid N-oleylamide.

PREPARATION OF LACTOBIONIC ACID N-OLEYLAMIDE 50 g of an aqueous solution containing 77% by weight of lactobionic acid (corresponding to 0.108 mol) was mixed with 200 ml of 2-ethoxyethanol in a distillation flask and stirred at 70° to 80° C. for about 1 hour. About 150 ml of an azeotropic mixture of 2-ethoxyethanol and water was then distilled off in a vacuum. After addition of a further 100 ml of 2-ethoxyethanol, the azeotropic distillation was continued to obtain a suspension of about 60 ml. The suspension was allowed to cool to about 50° C. Then, 25.9 g of oleylamine (corresponding to 0.098 mol) were dissolved in 20 ml of 2-ethoxyethanol and slowly added to the suspension by stirring. The mixture was then stirred at 50° C. for about 2 hours to obtain a nearly clear solution again. The mixture was then stirred at room temperature for about 12 hours. In the process, a suspension was formed again, which was stirred into 500 ml. of ethyl acetate. The white precipitate which was deposited in this process was filtered out under a gentle vacuum, washed with ethyl acetate and then dried at 40° to 50° C. in a vacuum drying oven. The yield of lactobionic acid N-oleylamide based on oleylamine was 85% by weight.

The remaining solvent mixture was combined with the azeotrope of 2-ethoxyethanol and water removed by distillation, and then separated again. To do this, the mixture of ethyl acetate, 2-ethoxyethanol and water was distilled at 100° C. through a column with a water separator. A two-phase mixture of ethyl acetate and water was obtained in the distillate receiver, from which the aqueous phase was removed with the water separator, while the organic ethyl acetate phase was fed back into the process again for the preparation of lactobionic acid N-oleylamide. After complete removal of water and ethyl acetate, the 2-ethoxyethanol remaining was distilled in a vacuum at about 80° C. and again, fed back into the preparation process.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A process for the preparation of aldobionamide, wherein organic solvents are circulated in a closed solvent cycle, said process comprising the steps of a) mixing an aldobionic acid or an aldobionic acid solution with an organic solvent capable of forming an azeotrope with water, b) removing water from the aldobionic acid by azeotropic distillation to obtain a soulution of aldobionolactone in said organic solvent and a water-containing azeotropic distillate;

c) reacting the aldobionolactone solution from step b) with an amine to obtain a solution or suspension of the aldobionamide in said organic solvent;

d) precipitating the aldobionamide by adding a further orqanic solvent to the solution or suspension from step c) and separating the precipitate to leave an orqanic solvent mixture;

e) combining the water-containing azeotropic distillate from step b) and the solvent mixture from step d), f) separating the combined mixture from step e) into water and orqanic solvent components, and g) feeding separated organic solvent components from step f) back into step a) or d).

2. A process according to claim 1, wherein an aqueous solution of aldobionic acid is mixed with the organic solvent.

3. A process according to claim 1, wherein the organic solvent is selected from the group consisting of cyclohexane, ethyl acetate, 2-methoxyethanol and 2-ethoxyethanol.

4. A process according to claim 1, wherein the organic solvent is 2-ethoxyethanol.

5. A process according to claim 1, wherein the amine is an alkylamine.

6. A process according to claim 5, wherein the alkylamine is a primary alkylamine having a chain length in the range of from 8 to 18 carbon atoms.

7. A process according to claim 1, wherein the amine is a primary amine.

8. A process according to claim 7, wherein the primary amine is a fatty amine.

9. A process according to claim 8, wherein the fatty amine is selected from the group consisting of coconut fatty amine, tallow amine, hydrogenated tallow amine and oleylamine.

10. A process according to claim 1, wherein aldobionic acid alkylamide is prepared.

11. A process according to claim 10, wherein the aldobionic acid alkylamide is lactobionic acid alkylamide.

12. A process according to claim 1, wherein said organic solvent capable of forming an azeotrope with water in step a) is 2-methoxyethanol or 2-ethoxyethanol, and separated 2methoxyethanol or 2-ethoxyethanol from step f) is fed back to step a).

13. A process according to claim 1, wherein the further organic solvent added in step d) to precipitate the aldobionamide is ethyl acetate, and separated ethyl acetate from step f) is fed back to step d).

14. A process according to claim 1, wherein the process is carried out continuously.

* * * * *